US012776227B2

(12) United States Patent
Kullmer et al.

(10) Patent No.: US 12,776,227 B2
(45) Date of Patent: Oct. 27, 2026

(54) EXTREMITY DUMMY AND METHOD FOR TESTING THE FUNCTIONING OF AN ORTHOSIS

(71) Applicant: Universitaet Paderborn, Paderborn (DE)

(72) Inventors: Gunter Kullmer, Altenbeken (DE); Britta Schramm, Paderborn (DE); Tommy Schafran, Unna (DE); Dirk Theodor Schraeder, Detmold (DE)

(73) Assignee: Universitaet Paderborn, Paderborn (DE)

( * ) Notice: Subject to any disclaimer, the term of this patent is extended or adjusted under 35 U.S.C. 154(b) by 537 days.

(21) Appl. No.: 18/032,556

(22) PCT Filed: Oct. 13, 2021

(86) PCT No.: PCT/EP2021/078252
§ 371 (c)(1),
(2) Date: Apr. 18, 2023

(87) PCT Pub. No.: WO2022/084112
PCT Pub. Date: Apr. 28, 2022

(65) Prior Publication Data

US 2023/0386365 A1 Nov. 30, 2023

(30) Foreign Application Priority Data

Oct. 23, 2020 (DE) ..................... 10 2020 127 967.1

(51) Int. Cl.
*G09B 19/00* (2006.01)
*A61F 5/01* (2006.01)
*G09B 23/30* (2006.01)

(52) U.S. Cl.
CPC ............ *G09B 23/30* (2013.01); *A61F 5/0111* (2013.01)

(58) Field of Classification Search
CPC ............................... G09B 23/30; A61F 5/0111
USPC .......................................................... 434/267
See application file for complete search history.

(56) References Cited

U.S. PATENT DOCUMENTS

2011/0208322 A1* 8/2011 Rifkin ....................... A61F 2/66 623/53
2015/0317917 A1* 11/2015 Fritz .................. G01M 17/007 434/267
2019/0328604 A1* 10/2019 Contreras-Vidal .......................... A61H 1/0244

* cited by examiner

*Primary Examiner* — Xuan M Thai
*Assistant Examiner* — Lisa H Antoine
(74) *Attorney, Agent, or Firm* — Norris McLaughlin, P.A.

(57) ABSTRACT

An extremity dummy includes a first and a second dummy section which are connected in an articulated manner by a joint element having at least one axis of rotation and also includes a sensor by which the angular position or angular change of the connected dummy sections with respect to the axis of rotation to which the sensor is provided can be measured. Preferably, a respective sensor is provided to each of the axes of rotation of the joint element. A method for testing an orthosis using the extremity dummy is also provided.

14 Claims, 6 Drawing Sheets

EXTREMITY DUMMY AND METHOD FOR TESTING THE FUNCTIONING OF AN ORTHOSIS

The invention relates to an extremity dummy, comprising a first and a second dummy section, which are connected in an articulated manner by way of a first joint element having at least one axis of rotation. The invention furthermore relates to a method for testing the function of an orthosis, which can be applied to an extremity, in particular a lower extremity of a patient, in particular for immobilizing the extremity.

The testing of orthoses, for example lower leg orthoses in conjunction with an extremity dummy, is known from the prior art, for example from the publication by D. Hochmann, "Prüfung von Unterschenkelorthesen (Testing of Lower Leg Orthoses)," in ORTHOPÄDIE TECHNIK 05/14, page 102 et seq.). This describes applying a lower leg orthosis to a lower leg dummy and exerting movements according to EN ISO 22675, which replicate conventional a heel/toe roll, on the orthosis using a testing device. For testing the orthosis, strain gauge-based sensors were provided on the orthosis itself in laminate layers and, in this way, the bending behavior of the orthosis as well as the fatigue properties or the lessening of rigidity over the time were found. It is also known from the publication by Wach, A., McGrady, L., Wang, M., and Silver-Thorn, B. (Apr. 30, 2018), "Assessment of Mechanical Characteristics of Ankle-Foot Orthoses" ASME., J Biomech Eng. July 2018; 140(7): 071007 to provide markers on the outside of the orthosis, by way of which displacement of the orthosis can be evaluated based on video.

The lower leg dummy used comprises a lower leg section and a foot section, which are connected by a joint. The foot section additionally enabled a rolling motion over the forefoot in the metatarsophalangeal joint.

An orthosis is a medical aid, in particular in the manner of an exoskeleton, frequently simply referred to as a splint, which is used, for example, for immobilizing, or only for stabilizing, relieving, or guiding extremities, or the torso, of a patient. It is known that orthoses are produced industrially or in what is usually an artisanal process by an orthopedic technician.

The present invention, similarly to the aforementioned prior art, relates to the field of application of lower leg orthoses and lower leg dummies, without being limited thereto. In principle, the extremity dummy according to the present invention can represent any extremity of a patient, and the orthosis can be applied to any such extremity.

The invention can specifically be used in the preferred field of application. It is known, for example, that patients with diabetes can develop diabetic foot syndrome, which, in a severe case, can result in collapse of the arch of the foot or even the need for amputation of the foot. So as to prevent this, therapeutic measures are aimed at immobilizing the affected foot by way of an orthosis that is applied to the foot and the lower leg. In doing so, it may generally be assumed that the better the immobilization by the orthosis, the greater is the success of the treatment.

The problem in this field of application, but also generally speaking, is that industrially manufactured orthoses, which are to fit a plurality of patients as well as possible, frequently do not offer sufficient function with regard to the immobilization on the particular patient-specific extremity.

In the aforementioned field of application, treatment success may thus not materialize, even if an orthosis is worn. There is reason to assume that patient-specifically manufactured orthoses provide better treatment success compared to industrially manufactured standard orthoses.

It is the object of the invention to provide an extremity dummy and a method for testing orthoses, which yield the option of being able to better assess the function of the orthosis than in the prior art, in terms of the effect thereof on the extremity. Even though the described prior art offers the option of assessing the rigidity of an orthosis under load, it does not allow testing as to the effects that the loaded orthosis exerts on the extremity, and consequently is factually not able to metrologically find the quality of the immobilization of the extremity. The invention is to provide this option.

According to the invention, this is achieved in the extremity dummy of the type mentioned at the outset in that a sensor, by way of which the angular position or angular change of the connected dummy section with respect to the assigned axis of rotation can be measured, is assigned to the at least one axis of rotation, and preferably each of several axes of rotation, of the joint element.

In contrast to the dummies known from the aforementioned publications, such a dummy makes it possible to measure the change in position of the dummy sections, for example changes in angle, or an absolute angle, with respect to one another, for example when the dummy is fitted with an orthosis, and this orthosis is loaded. This allows conclusions as to the specific effectiveness of the orthosis, at least on the dummy, which, in turn, allows conclusions as to the effectiveness on the specific extremity of a patient with respect to the immobilization of an extremity.

This opens up a method according to the invention for testing the function of an orthosis that can be applied to an extremity of a patient, in particular for the purpose of immobilizing the extremity, in which the orthosis to be tested is applied to an extremity dummy according to the invention representing the extremity of the patient to which the orthosis can be applied, and a force is exerted on at least one of the dummy sections of the extremity dummy so as to displace this dummy section in relation to at least one other dummy section with which an articulated connection is made by way of a joint element, against the action of the orthosis, and the position or change in position of the dummy sections with respect to one another is measured using at least one sensor, which is assigned at least to one joint axis of the joint element. For example, it may then be provided that the measurement values of the position, or change in position, are acquired as a function of the exerted force or a position parameter, preferably an angular position, of the actuator exerting the force. Based on the acquired measurement values, it is thus possible to assess more easily and more reliably not only the effectiveness of the orthosis per se, but the effectiveness of the orthosis on the extremity dummy, or specifically on the extremity of the patient.

In particular in the preferred use during the treatment of diabetic foot syndrome, it is possible to state generally speaking that the effect of a tested orthosis is improved the smaller the changes in position are when a force is exerted on a dummy section of the extremity dummy. This will generally apply to all applications of an orthosis in which the orthosis is intended for the immobilization of extremities.

It is preferably provided in the case of the extremity dummy that the same comprises a third dummy section, which is connected in an articulated manner to the second dummy section by way of a second joint element, and preferably a joint element having only one axis of rotation, wherein a sensor, by which the angular position or angular change of the dummy sections connected to the second joint element with respect to the assigned axis of rotation can be measured, is assigned to the at least one, and preferably exactly one, axis of rotation of the second joint element.

An extremity dummy of the invention can form a lower leg dummy for the preferred application, wherein the first dummy section represents a lower leg section of a lower leg extremity, and the second dummy section represents a foot section, in particular a midfoot section and/or a hindfoot section of a lower leg extremity, and the first joint element represents the ankle joint, and in particular the upper and lower ankle joints.

In the aforementioned preferred refinement, the third dummy section can represent a toe section of a foot extremity, and the second joint element can represent the midfoot joint row.

In the case of the joint elements, it is preferably provided that these replicate the physiological function of the represented joint, in particular in that the at least one joint axis of each joint element is oriented as is the case on the actual joint in a person, or on average in a plurality of persons. It may also be provided here to simulate a mobility in a physiological joint of the person, which in particular is more complex than just one axis, by coupling at least two joint axes in the joint element of the extremity dummy.

In the first joint element, which represents the ankle joint, it may be provided that the joint element has a first joint axis that, in the case of an assumed normally standing position of the extremity dummy corresponding to the standing position of a person, extends from medial to lateral, and in particular is oriented horizontally and perpendicularly to the transversal plane. Instead of a horizontal orientation, it is also preferably possible for an orientation of 74 to 94 degrees, preferably 82 degrees, with respect to the sagittal plane to be provided, which corresponds to mean orientation values acquired in a plurality of persons. This joint axis represents the upper ankle joint.

The same joint element can have a further joint axis, which represents the lower ankle joint. This joint axis can preferably be oriented in an angular range of 4 to 47 degrees, and preferably 23 degrees, with respect to the sagittal plane, and in the range of 20 to 69 degrees, preferably 42 degrees, with respect to the horizontal plane.

In the second joint element, which connects the toe section to the midfoot and/or hindfoot section, a single joint axis can preferably be provided, which in particular is situated centrally in the toe section, preferably in the horizontal plane, and preferably is inclined in a range of 53 degrees to 73 degrees, in particular 62 degrees, with respect to the sagittal plane. Using such an axis, it is possible to replicate the mobility of all toes and the rolling motion of the foot over the toes on the extremity dummy of the invention.

In general, existing anatomic data may be referred to for orienting the joint axes in the respective joint elements.

The extremity dummy can preferably be designed so that the first dummy section, representing the lower leg section, at the upper end thereof, comprises a force introduction connection, by way of which a force can be introduced into the dummy section in the axial and/or radial direction of the lower leg section, which in particular replicates the weight of a patient, and/or a force can be introduced into the dummy section by which the dummy section can be twisted about the axial extension thereof.

This force introduction connection preferably comprises a housing element, which is non-rotatably connected to the first dummy section in which a shaft element is rotatably mounted, wherein a sensor is provided, by which the angular position or relative rotation between the shaft element and the housing element can be measured, wherein preferably the shaft element can be at least temporarily non-rotatably fixed relative to the housing element, or at least can be inhibited from carrying out a rotation.

In the test method according to the invention, it may be provided that the extremity dummy, prior to or after applying the orthosis, is inserted into a testing device, wherein the testing device comprises at least one actuating element which can be actuated by way of an actuator and by which a force is exerted on at least one of the dummy sections. Such a procedure can be provided, regardless of the preferred application, using any type of extremity dummy so as to check the function of a particular type of orthosis on the extremity dummy.

In the preferred application in which the extremity dummy represents a lower leg extremity and orthoses provided for lower legs are to be tested, the invention can preferably provide that the testing device comprises a tread element on which the at least one dummy section including the applied orthosis is placed, which represents the midfoot region or the hindfoot region and/or toe region, and that the testing device comprises a retaining element, by which a retaining, twisting or a weight-simulating force is exerted on the upper end of the dummy section representing the lower leg section. The upper end, in this case, can be the aforementioned force introduction connection, for example. A force applying a load on the lower leg section in the axial extension thereof can, for example, be exerted on the aforementioned shaft. A force twisting the lower leg section can, for example, be exerted on the housing of the force introduction connection or on the rotationally inhibited or rotationally fixed shaft.

In a first possible test execution, it may then be provided, for example, that the tread element is pivoted about an axis that is parallel to the tread, preferably a horizontal axis, in particular so as to simulate a heel/toe roll during walking. Forces that can typically occur while a patient is walking are exerted by the tread element on the orthosis and, via the orthosis, on the extremity dummy.

In a second possible manner of carrying out the test, it may be provided that the tread element, prior to a force being introduced on the upper end of the dummy section representing the lower leg section, is fixed in an angular position that corresponds to a predetermined phase of the heel/toe roll during walking, and subsequently the upper end of the dummy section representing the lower leg is loaded with a force, in particular the weight of a patient or a mean weight common for a person. In this way, it is possible to deliberately exert forces on the orthosis and the extremity dummy during various walking phases.

It is also conceivable to twist the foot, according to the natural position of the foot, outwardly by a certain angle by way of the rotatable force introduction point so as to then carry out a functional test.

A further, third manner of carrying out the test can provide that the dummy section representing the midfoot region or hindfoot region and/or toe region is fixed on the tread element indirectly via the orthosis, non-rotatably about the longitudinal axis of the lower leg section, and a force twisting the dummy section about the longitudinal axis thereof is exerted on the dummy section representing the lower leg section. Due to the universal joint-like connection between the lower leg section and the midfoot/hindfoot section, it is possible, in the region of the foot, for tilting to occur with torsion of the lower leg, which is to be avoided in particular with diabetic foot syndrome and can therefore represent a particularly important test criterion.

Likewise, other manners of carrying out the test are possible, which are not exhaustively described here.

In all possible test executions, the invention may provide that the angular position and/or angular change of at least one dummy section with respect to another is measured, using the at least one sensor, in the joint element connecting these dummy sections, in particular as a function of the applied force and/or as a function of a position parameter, preferably an angular position, of the actuator exerting the force. For example, the angular position of the tread element can be detected here. The applied force can, for example, be the force generated by way of the tread element and/or the force introduced into the force introduction element of the lower leg section, which, for example, can simulate the weight of a patient. The respective sensors can be connected to a measuring electronics unit so as to acquire and store the measurement values, in particular as a function of the aforementioned force or the position parameter. The measuring electronics unit can likewise carry out the activation of the at least one actuator for exerting a force or for adjusting the tread element.

Both the extremity dummy and the orthosis can be implemented as a respective standard element in terms of the design, which in particular is adapted in each case as well as possible to the anatomy of a plurality of persons. This can be achieved, for example, when the orthosis and/or the extremity dummy are manufactured based on the averaged anatomical data of a plurality of persons.

In a preferred embodiment, the invention can provide that the actual anatomical circumstances of the patient for whom the orthosis is intended are taken into consideration in the orthosis and/or in the extremity dummy. In this way, in the test method, it is possible to ascertain, in advance, the effectiveness of the orthosis on the actual extremity of the patient, with enhanced accuracy.

It may preferably be provided that at least one of several dummy sections, and preferably each dummy section, is at least regionally, in particular at least in such regions which can be contacted by an orthosis, and preferably completely, designed as a function of, and preferably corresponding to, the individual shape of the section corresponding to the dummy section or the region corresponding to the region of the dummy section on the extremity of a patient.

In this way, an enhanced adaptation of the extremity dummy to the actual body extremity of the later orthosis wearer is achieved.

An extremity dummy that is designed as a function of the individual shape of the section corresponding to the dummy section on the extremity of a patient can be produced, for example, so that the extremity dummy is assembled from several dummy sections, wherein each dummy section to be used is selected from a set of dummy sections, which in particular all represent the same extremity section, and dummy sections of varying sizes or types are present in each set.

For example, a set of lower leg sections may be present in which different sizes or types are present insofar as the lower leg sections, for example, represent different body sizes or size levels (such as S, M, L, XL) or differently thick calf muscles or the like. For example, different foot sizes (shoe sizes) and/or different foot shapes, such as, for example, for taking into consideration splay foot, flat foot, high arch foot, and the like, may be present in a set in the case of the midfoot dummy sections.

After selecting the dummy section that is best-suited for the specific patient from a particular extremity section set, the dummy sections can be connected, preferably by way of the joint elements, for example using a screw connection.

Even though the above-described procedure achieves improved customization as a function of the anatomy of the patient, it does not yet achieve customization corresponding to the anatomy.

The invention can provide, for example, that at least one of the dummy sections, and preferably each dummy section, of the extremity dummy, is designed, in particular shaped, in such a way that the shape thereof, at least in regions, and in particular overall, very specifically corresponds to the shape of corresponding section/region on the actual extremity of the patient. The respective shape-corresponding dummy section of the extremity dummy according to the invention is thus preferably, at least in regions, identical, in terms of the shape, to the corresponding section on the extremity of the patient.

Here as well, after the dummy sections have been produced for the specific patient, the dummy sections are connected to one another so as to form the overall extremity dummy, preferably by way of the joint elements, for example using a screw connection.

It may likewise be provided, in all possible embodiments of the customization of the extremity dummy, to select the joint elements in each case from sets comprising several different joint elements, so as to also increase a degree of customization with regard to the joint elements. The customization here can, for example, take place with respect to the orientation of the joint axes.

Another option for achieving improved customization can provide that at least one of the dummy sections of the extremity dummy, and preferably each dummy section, comprises an attachment region, on which at least one shaped element, and preferably several shaped elements next to one another, can be attached, wherein the respective shaped element is either designed corresponding to the individual shape of the region corresponding to the shaped element on the extremity of a patient or is selected from a set of several shaped elements having differing sizes or being of differing types. For example, a set can comprise several shaped elements having incrementally differing sizes.

An attachment region can, for example, be designed as a bar, which preferably extends between the ends thereof situated in the longitudinal direction of the dummy section and, for example, connects two joint elements or connects one joint element to a force introduction element. It is then possible to place the shaped elements on such a bar, preferably in a torsion-proof manner, and in particular in a form-locked and/or force-fit manner. The bar is preferably designed to have a non-circular cross-section, and preferably is designed to have a polygonal cross-section.

A respective shaped element can have a one-piece design. The shaped element then, for example, extends around the bar in the circumferential direction by less than 360 degrees, preferably, however, more than 270 degrees, so as to provide an opening for the placement on the bar. It may also be provided that a shaped element has a two-piece or multi-piece design, and preferably is closed over the circumference when assembled. In the separated state, the shaped element can then be attached to the bar and joined, and thereafter can preferably completely surround the bar.

With respect to the aforementioned embodiments, the invention may provide, for example, that a respective shape-corresponding dummy section or a respective shape-corresponding shaped element is designed as a component that is additively produced, in particular by way of 3D printing, as a function of data representing the corresponding section on the extremity of a patient.

It may likewise be provided that a respective shape-corresponding dummy section or a respective shape-corresponding shaped element is designed as a component that is produced from a blank by way of machining, as a function of data representing the corresponding section on the extremity of a patient.

Such data for the two aforementioned embodiments can, for example, be acquired by an optical scan of the extremity, for example by a laser scan.

Furthermore, it may likewise be provided that a respective shape-corresponding dummy section or a respective shape-corresponding shaped element is designed as a component that is molded from a negative mold corresponding to the appropriate section on the extremity of a patient. Such a negative mold can, for example, create an impression of the patient extremity using an impression compound, for example a plaster impression, which is subsequently poured so as to create the dummy section or the shaped element.

In particular the shape-corresponding design of the extremity dummy in at least one dummy section, and preferably all dummy sections, offers the best option for testing the effectiveness of an orthosis, in particular when the same itself is adapted to the anatomy, which is to say the shape of the extremity of the patient to which the orthosis is to be applied.

Preferably, it may be provided that the extremity dummy is not only designed so as to have a shape that corresponds to the extremity of a patient, but also as a function of the orthosis that is individually designed for the same patient.

An orthosis will thus, for example, not completely surround an extremity of the patient, for example already for the sole reason of being able to apply the same to the extremity or to offer sufficient venting. This means that regions are present in an orthosis that do not rest against the extremity, or where the orthosis is open. The orthosis is necessarily not adapted to the extremity of the patient in such regions. The invention can thus provide that, in those regions where the orthosis does not have a design that corresponds, in terms of the shape, to the extremity of the patient, the extremity dummy in the dummy sections thereof or the shaped elements likewise does not have a shape-corresponding design.

Another embodiment can provide that various dummy sections and/or various regions of a dummy section or various shaped elements have differing deformability or rigidity, in particular by being made of materials having differing moduli of elasticity or being configured with differing reinforcement structures, and/or have differing surface properties, in particular due to differing surface coatings. For example, the surface of a dummy section or shaped element can be covered with a textile, in particular to better simulate the friction between the orthosis and the skin or to replicate the displaceability of the skin surface.

In this way, adaptation to different anatomic circumstances of the patient is also possible.

The invention may furthermore provide that opposing joint elements of a dummy section or a mutually opposing force introduction connection and joint element of a dummy section are connected by way of a reinforcement element having a higher rigidity than the material of the dummy section surrounding the reinforcement element.

Such a reinforcement element can also form the aforementioned attachment region, for example a bar for attaching at least one shaped element.

The above-described extremity dummy in the particularly preferred method opens up the possibility that the extremity dummy is individually adapted, at least in regions, to the extremity of a patient, so that the extremity dummy, in the adapted regions, corresponds to the shape of the extremity of the patient, wherein in particular the orthosis to be tested is also individually adapted, at least in regions, to the extremity of a patient, in particular by the orthosis being designed, at least in regions, as a negative mold that corresponds to the shape of the extremity of the patient, and the orthosis, and in particular the adapted orthosis, is applied to the adapted extremity dummy. The extremity dummy is preferably only individually adapted to the extremity of a patient in those regions in which the orthosis is also being adapted.

In this case, the test of the adapted orthosis on the adapted extremity dummy reflects the behavior of the orthosis later on the extremity of the patient particularly well. The functional effectiveness of the orthosis with respect to an immobilization of extremities can thus be checked or confirmed particularly reliably, in particular when, as a result of the adaptation of the dummy sections in terms of the modulus of elasticity of the material thereof and possible surface coatings to the extremity of the patient, the soft tissue behavior of the extremity of the patient is also replicated.

Exemplary embodiments of the invention will be described hereafter.

The following is a brief description of the drawings.

Figure 1:
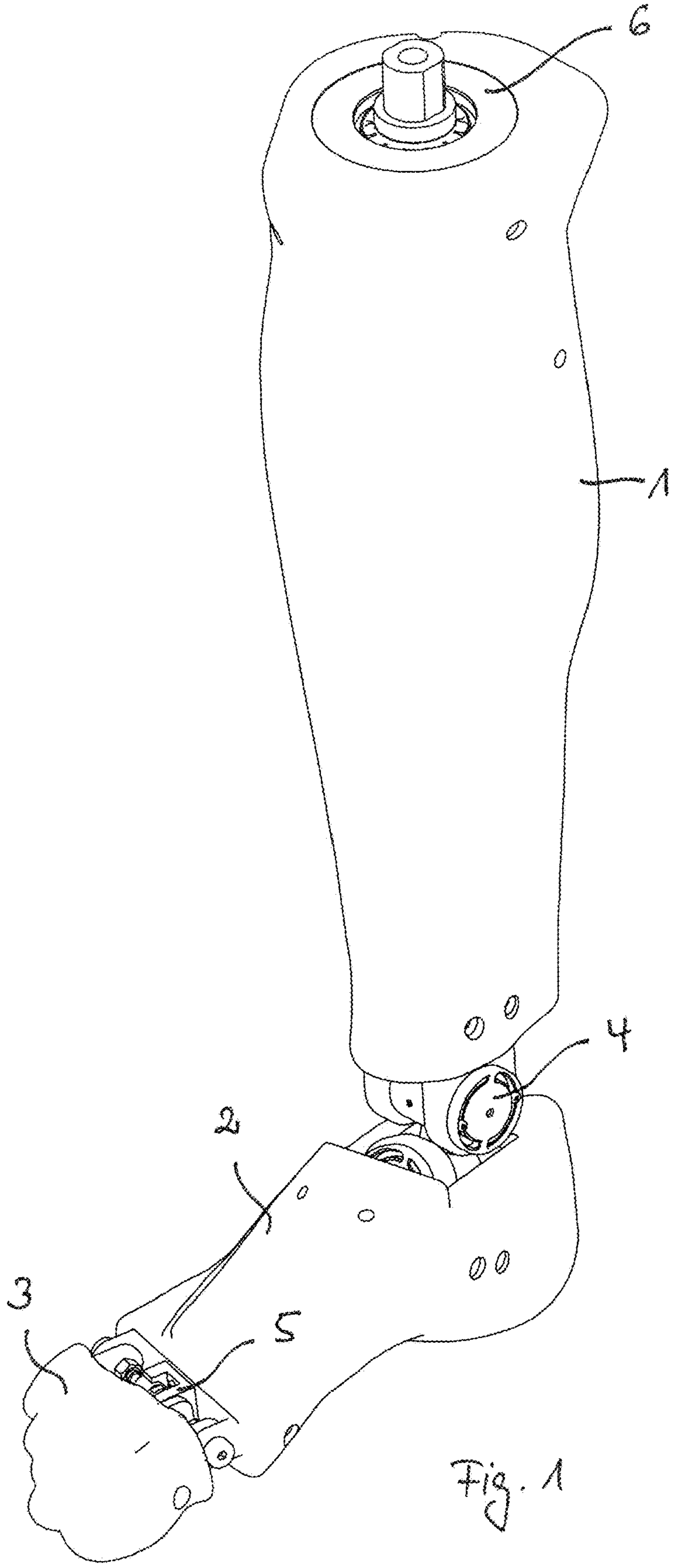
FIG. 1 is a perspective view of a lower leg extremity dummy of the invention.

FIG. 1 shows an overall overview of an extremity dummy of the invention which, in this example, represents a lower leg. The extremity dummy comprises a first dummy section 1, which forms the lower leg section, a second dummy section 2, which forms the midfoot section, and a third dummy section 3, which forms the toe section of a foot.

The first and second dummy sections 1, 2 are connected in an articulated manner by way of a first joint element 4. The second and third dummy sections 2, 3 are connected by way of a second joint element 5. A force introduction element 6 is provided at the upper end of the first dummy section 1.

Figure 2:
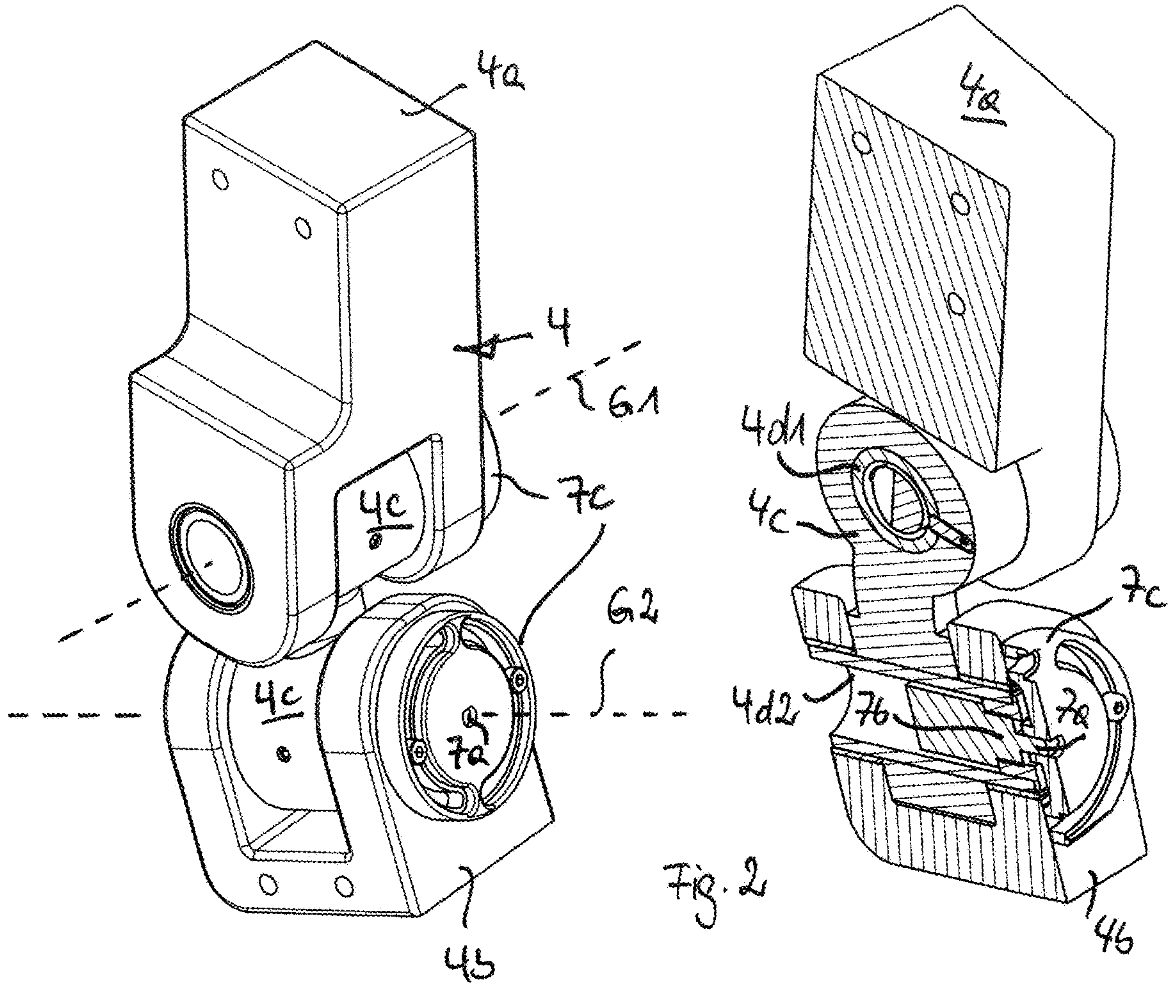
FIG. 2 shows a joint element of the embodiment of FIG. 1 in greater detail.
Figure 3:
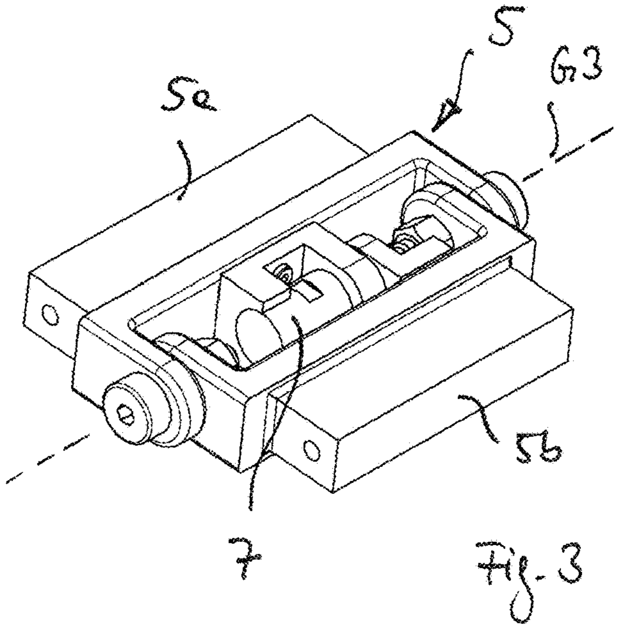
FIG. 3 shows another joint element of the embodiment of FIG. 1 in greater detail.
Figure 4:
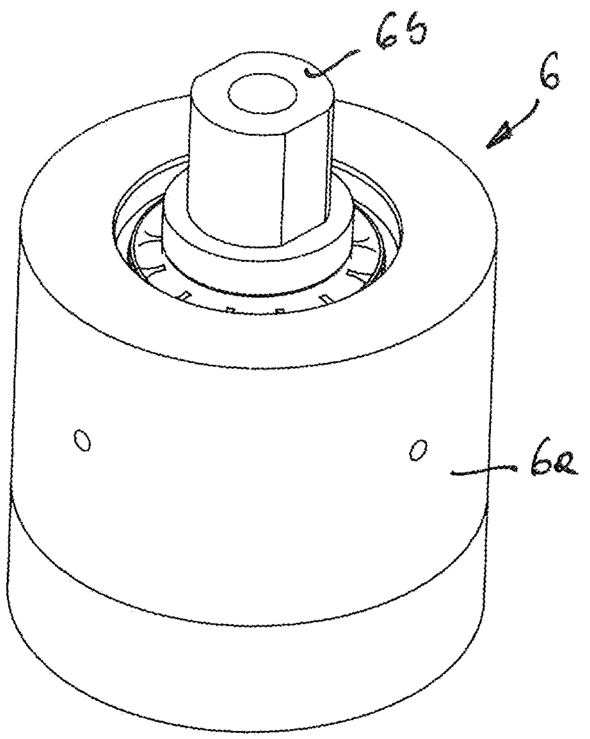
FIG. 4 shows a force introduction element of the embodiment of FIG. 1 in greater detail.
Figure 4:
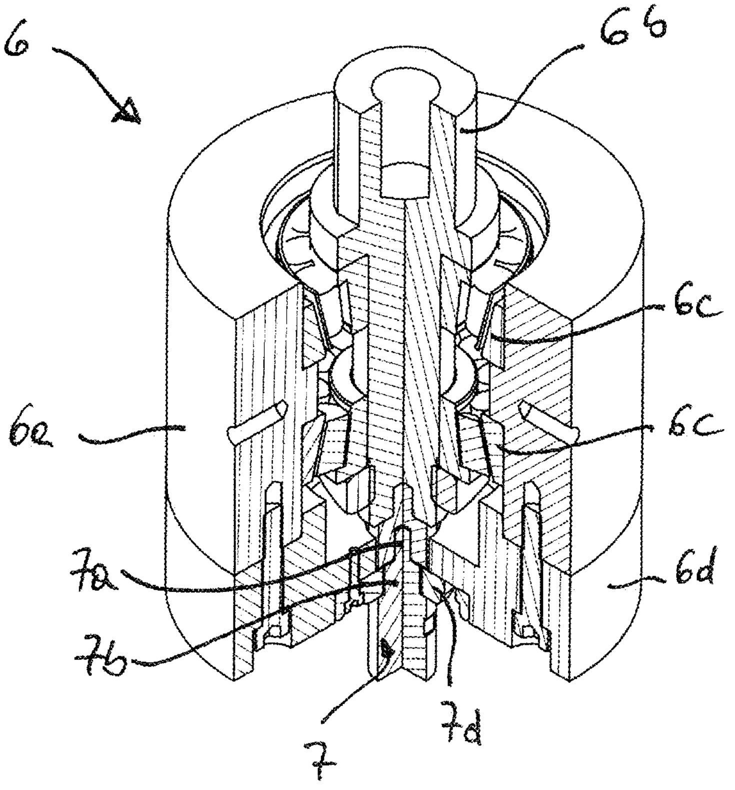

FIGS. 2 to 4 show the elements 4, 5 and 6 in greater detail. The first joint element 4 according to FIG. 2 has a first joint axis G1 and a second joint axis G2. These two joint axes simulate the function of the upper and lower ankle joints of the person.

The second joint element 5 according to FIG. 3 has only one joint axis G3 here, to simulate the toe mobility.

The axial orientation of the joint axes can, in each case, be made as described in the general part of the description.

For each of the joint axes, each joint element 4, 5 comprises a sensor 7, by way of which the angular position or the angular change about the respective joint axis can be measured and metrologically acquired. Such sensors can infer the respective angular position via the change in potential of the voltage, for example using the Hall effect. This requires a hard-wired electronic power supply for the sensors. A suitable sensor is, for example, one included in the Euro-CM RT series from Variohm.

On the joint element 5, the stator of the sensor 7 is connected to one of the joint element parts that are disposed around the joint axis, and the rotor of the sensor is connected to the respective other joint element part.

For example, the ankle joint comprises the two joint element parts 4*a*, 4*b* as well as a joint element part 4*c* connecting the two joint element parts 4*a*, 4*b*. The connecting joint element part 4*c* is non-rotatably connected to a respective hollow shaft 4*d*1 and 4*d*2 about the respective axis of rotation G1 and G2. A respective sensor 7 is disposed in each of the two hollow shafts 4*d*1 and 4*d*2. The stator 7*b* of the sensor 7 is non-rotatably attached to the hollow shaft 4*d*1 and 4*d*2, for example by way of a threaded connection. The rotor 7*a*, at the end thereof, rests non-rotatably, for example in a form-locked manner, in a disk-shaped adjusting element 7*c*, by way of which the angular position of the rotor 7*a* can be influenced, for example so as to set a reference position or neutral position, and which can be non-rotatably attached to the joint element part 4*a* or 4*b*. In this way, it is made possible to acquire the angular positions or changes between the joint element parts 4*a* and 4*c* or 4*b* and 4*c*.

Such sensors can, for example, be angle encoders, which are connected to a measurement electronics unit.

Each joint element 4, 5 comprises two joint element parts 4*a*, 4*b* or 5*a*, 5*b*, which are disposed through the axes of rotation or around the axis of rotation and which are connected, for example by way of a screw joint, to the dummy sections situated around the respective joint element 4, 5.

The force introduction element 6 shown in FIG. 4 comprises an outer housing 6*a*, in which a shaft 6*b* is rotatably mounted, for example by way of two ball bearings or cylindrical roller bearings 6*c*. A sensor 7 is likewise disposed here at the bottom of the housing 6*a*, by which the angular position or change of the shaft 6*b* in the housing 6*a* can be measured. The housing 6*a* is non-rotatably attached, for example screwed, to the dummy section representing the lower leg. Here, the rotor 7*a* of the sensor can be non-rotatably connected to the shaft 6*b*, and the stator 7*b* can be indirectly connected to the housing 6*a* via the stator flange 7*d* and the attachment ring 6*d* of the housing 6*a*.

Using a force that acts axially or also at an angle different from 0 degrees with respect to the shaft axis on the shaft 6*b*, weight loading of the extremity dummy can be simulated, for example by the weight of the patient who later is to wear the orthosis to be tested. It may also be provided to exert a force greater than this weight.

Torsion of the lower leg section can be achieved by a force that acts on the housing 6*a* in the circumferential direction about the axis of rotation of the shaft 6*b*. This force preferably acts directly on the housing 6*a* or indirectly on elements connected to the housing 6*a*.

Figure 5:
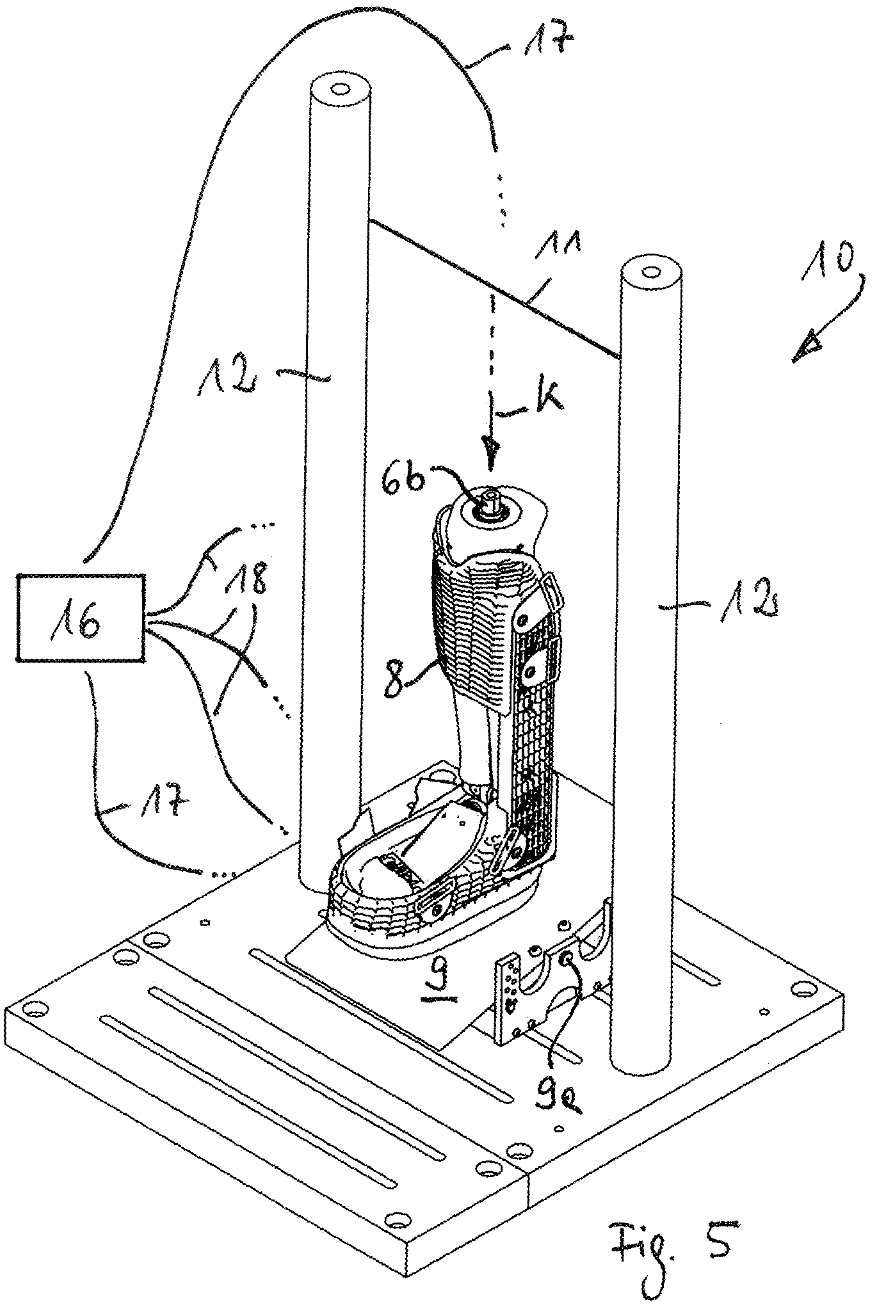
FIGS. 5, 6 and 7 are perspective views showing a portion of a testing device in which the extremity dummy of FIG. 1 and an orthosis applied thereto are inserted.

FIG. 5 shows portions of a testing device 10 in which an extremity dummy including an applied orthosis 8 is inserted, so that the dummy sections 2 and 3, which represent the midfoot and toes, rest on a tread element 9 of the testing device 10 via the orthosis 8. In this embodiment, the tread element 9 is pivotably mounted in two bearing brackets about the horizontal pivot axis 9*a*. The pivoting can be carried out, for example, by way of an actuator, which is not shown. The actuator can be activated by a measuring device 16, for example, by which the measurement values of the sensors 7 are also acquired and stored. As is shown in FIG. 5, the measuring device 16 can be connected for this purpose, by control cables 17, to the actuators so as to move the tread element 9 and/or generate the force K. Using measuring cables 18, the measurement values can be transmitted from the sensors 7 to the measuring device 16. This is only shown in FIG. 5, but applies likewise to the other figures.

To ensure that the extremity dummy is held securely in the testing device 10, a retaining device 11, which is only shown schematically here and can be attached to the columns 12, engages on the upper end of the extremity dummy and exerts a retaining and/or weight-exerting force K on the shaft 6*b*. The exertion of the force on the shaft 6*b* can already be carried out in the direction of the shaft axis in this example.

It is now possible to carry out a test so that, for example under the action of the force K, the angle of the tread element 9 about the axis of rotation 9*a* is continuously adjusted in a predetermined angular range.

As an alternative, it is also possible to predefine a predetermined fixed angular position of the tread element 9 and to thereafter load the extremity dummy using a force K on the force introduction element 6. The angular position is preferably adjusted via the joint axis 9*a*.

Figure 6:
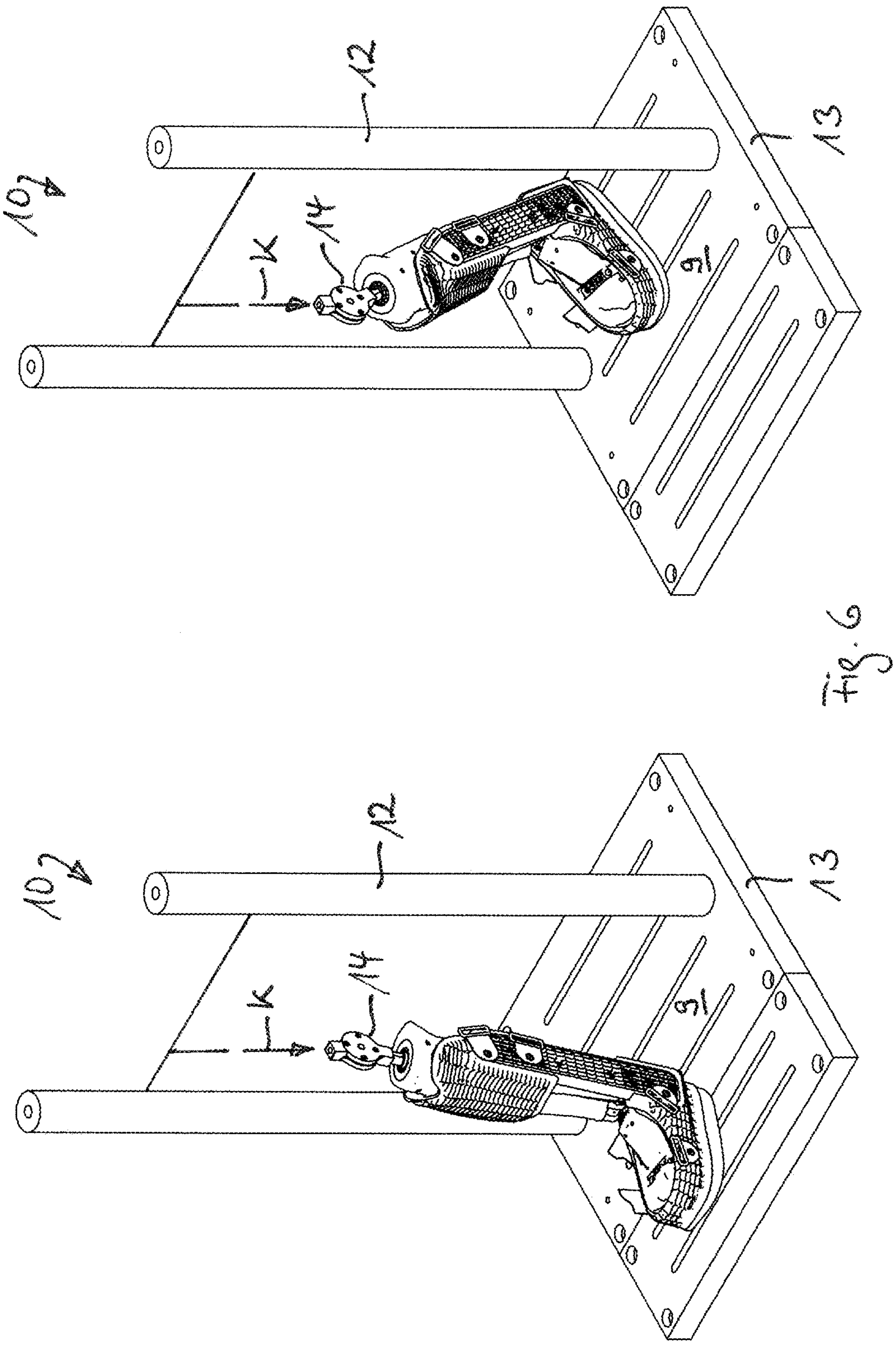

According to FIG. 6, it may also be provided that the pivotable tread element 9 is dispensed with, and a fixed tread element is formed by the base plate 13 of the testing device 10. In this embodiment, it is provided to introduce the force K that acts on the shaft 6*b* of the force introduction element indirectly into the shaft 6*b* via a joint element 14. This joint element 14 can simulate the knee joint function in one axis, for example.

It may then be provided to exert the force indirectly via the joint element 14 on the upper end of the dummy section, and in particular on the shaft 6*b* of the force introduction element 6, while the joint position of the joint element 14 is adjusted incrementally or continuously, or the joint position, prior to the force introduction on the upper end of the dummy section representing the lower leg section, is fixed in an angular position corresponding to a predetermined phase of the heel/toe roll while walking, and subsequently the upper end is loaded with a force.

One embodiment can provide that, in the arrangement according to FIG. 6, the joint element 14 is displaced in the walking direction by an actuator, so as to simulate a walking motion, in particular while a force is being exerted.

In these test versions, the angle or the angular change in at least one of the axes of rotation, and preferably all axes of rotation, of the joint elements 4, 5, and possibly also in the force introduction element 6, is acquired by the sensors 7 and recorded by a measurement electronics unit, preferably as a function of the angular position of the tread element and/or the acting force K.

In general, the measuring electronics unit can be connected, for example via cables, to the sensors 7 in all possible embodiments. It is also possible to use wireless sensors having a radio connection to the measuring electronics unit.

Figure 7:
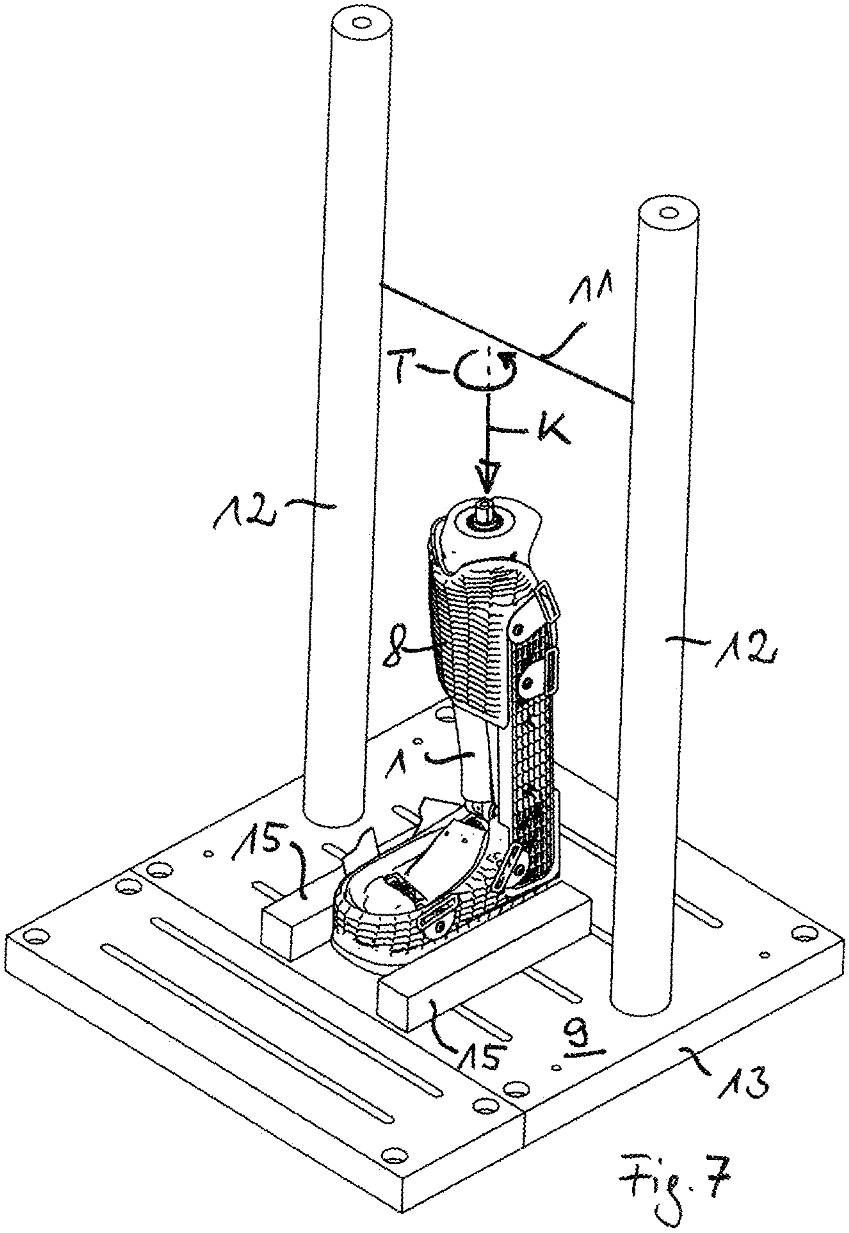

In FIG. 7, the extremity dummy is held at the top as in FIG. 5 and loaded with a force K. In this case, the tread element 9 is again formed by the base plate 13 of the testing device 10 and cannot be pivoted. On this tread element 9, the extremity dummy, together with the applied orthosis 8, is fixed by the lateral jaw elements 15 to prevent twisting, in particular with respect to the longitudinal axis of the lower leg section 1.

It is now possible to exert a torsional force T about the lower leg longitudinal axis, which can correspond to the direction of the force K, on the upper end of the lower leg section 1 of the extremity dummy, for example by a lever that is loaded by a force and engages on the housing 6*a* of the force introduction element 6.

The angle or angular change that results as a function of the torsional force T and/or the force K is then measured, at least in the axes of rotation G1 and G2 of the joint element 4.

When the extremity dummy including the orthosis 8 is disposed on a pivotable tread 9 according to FIG. 1, the same test could also be carried out for different pivot angles of the tread element 9.

Using the embodiments shown by way of example, a certain orthosis 8 can be tested in conjunction with an extremity dummy with respect to the functional effect thereof with respect to the immobilization of an extremity. Preferably, industrially manufactured standard orthoses can be compared, in terms of the effect, to patient-specifically manufactured orthoses 8, in particular when the extremity dummy is also adapted to the patient, as was described at the outset.

The invention claimed is:

1. An extremity dummy which forms a lower-leg dummy, comprising a first and a second dummy section which are connected in an articulated manner by a first joint element having at least two axes of rotation and representing an ankle joint, wherein a. the first dummy section represents a lower-leg section of a lower-leg extremity, and b. the second dummy section represents a metatarsal section and/or rear foot section of a lower extremity, wherein the first joint element represents an upper and lower ankle joint and is configured to simulate mobility in a physiological human joint by coupling of the at least two axes of rotation of the first joint element, and wherein each of the at least two axes of rotation of the first joint element is provided with a respective sensor configured to measure an angular position or change an angle of the first joint element with respect to the axis of rotation to which the sensor is provided, and the first dummy section has, at its upper end, a force introduction connection configured to introduce a force into the first dummy section to twist the first dummy section about an axis thereof.

2. The extremity dummy according to claim 1, wherein a third dummy section is provided which is connected in the articulated manner to the second dummy section by a second joint element having only one axis of rotation, another sensor is provided to the only one axis of rotation, the other sensor being configured to measure an angular position or angular change of the second and third dummy sections connected to the second joint element with respect to the only one axis of rotation.

3. The extremity dummy according to claim 2, wherein: the third dummy section represents a toe section of the lower leg extremity and the second joint element represents a row of metatarsal joints.

4. The extremity dummy according to claim 2, wherein each of the dummy sections is, at least in regions thereof which are configured to be completely contacted by an orthosis, of a shape corresponding to a shape on a corresponding extremity of a patient.

5. The extremity dummy according to claim 4, wherein the extremity dummy is assembled from sets of the first, second and third dummy sections same of varying sizes and/or types and representing a same extremity section.

6. The extremity dummy according to claim 4, wherein each of the dummy sections comprises an attachment region configured for attachment thereto of a plurality of shaped elements next to one another, the shaped elements being a. configured corresponding to a shape of the region corresponding to the shaped element on the extremity of a patient or b. selected from a set of a plurality of shaped elements having differing sizes or being of differing types, the set including a plurality of shaped elements having incrementally differing sizes.

7. The extremity dummy according to claim 4, wherein the shape of the dummy section corresponding to the shape on an extremity of the patient:

a. additively produced by 3D printing as the function of data representing the corresponding shape on the extremity of the patient;

b. produced from a blank by machining as the function of data representing the corresponding shape on the extremity of the patient; or c. molded from a negative mold corresponding to the shape on the extremity of a patient.

8. The extremity dummy according to claim 2, wherein at least one of the dummy sections or at least one region thereof differs from other of the dummy sections or from the at least one region thereof in a. deformability or rigidity by being made of materials having differing moduli of elasticity or being configured with differing reinforcement structures, and/or b. surface properties due to differing surface coatings.

9. The extremity dummy according to claim 2, wherein the first and the second opposing joint elements at the second dummy section or a mutually opposing force introduction connection and the first joint element at the first dummy section are connected by a reinforcement element having a higher rigidity than the material of the dummy section surrounding the reinforcement element.

10. A method for testing a function of an orthosis configured to be applied to an extremity of a patient, comprising a. applying the orthosis to be tested to an extremity dummy according to claim 3 representing the extremity of the patient to which the orthosis is configured to be applied; and b. exerting a force on at least one of the dummy sections of the extremity dummy so as to displace, against an action of the orthosis, the at least one of the dummy sections in relation to at least one other of the dummy sections with which an articulated connection is made by first or second joint element; and c. measuring a position or change in position of the dummy sections with respect to one another with at least one of the sensors as the function of the exerted force and/or of an angular position of an actuator exerting the force.

11. The method according to claim 10, further comprising, prior to or after the application of the orthosis to the extremity dummy, inserting the extremity dummy into a testing device, the testing device comprising at least one actuating element configured to be actuated by the actuator to exert the force on at least one of the dummy sections.

12. The method according to claim 11, wherein a testing device comprises a tread element on which the first and/or the second dummy section including the orthosis applied thereto is placed, and the testing device further comprises a retaining element configured to exert a retaining, twisting or weight-simulating force on an upper end of the first dummy section, a. the tread element is pivoted about an axis that is parallel to the tread so as to simulate a heel/toe roll while walking, b. the tread element, prior to the force introduction on the upper end of the dummy section, being fixed in an angular position corresponding to a predetermined phase of a heel/toe roll while walking, and subsequently the upper end being loaded with the weight-simulating force, c. the weight-simulating force being exerted indirectly, via a joint element on the upper end of the first dummy section, on a shaft of a force introduction element, while a joint position of the joint element is incrementally or continuously adjusted, or the joint position, prior to the force introduction on the upper end of the dummy section, being fixed in an angular position corresponding to a predetermined phase of the heel/toe roll while walking, and subsequently the upper end of the first dummy section being loaded with the weight-simulating force, or d. the second and/or third dummy section being fixed on the tread element non-rotatably about a longitudinal axis of the first dummy section, and a force twisting the dummy section about the longitudinal axis thereof being exerted on the first dummy section, an angular position and/or angular change of at least one of the dummy sections with respect to another being measured, as a function of the applied force, by at least one of the sensors.

13. The method according to claim 10, wherein the extremity dummy is adapted, at least in regions thereof, to a corresponding extremity of a patient, so that the extremity dummy, in the adapted regions, corresponds to the shape of the extremity of the patient, also the orthosis to be tested is adapted, at least in regions thereof, to the corresponding extremity of the patient, the orthosis being configured, at least in said regions thereof, as a negative mold that corresponds to the shape of the extremity of the patient, and the thusly adapted orthosis being applied to the adapted extremity dummy.

14. The method according to claim 13, wherein the extremity dummy is adapted to the extremity of the patient only in those regions in which the orthosis is also adapted.

* * * * *